United States Patent [19]

Herrmann

[11] Patent Number: 4,799,599
[45] Date of Patent: Jan. 24, 1989

[54] SPECIMEN CUP AND CAP ASSEMBLY FOR CLINICAL ANALYZER

[75] Inventor: Raymond J. Herrmann, Westlake, Ohio

[73] Assignee: Ciba Corning Diagnostics Corp., Medfield, Mass.

[21] Appl. No.: 404,477

[22] Filed: Jul. 30, 1982

[51] Int. Cl.$^4$ .............................................. B65D 51/16
[52] U.S. Cl. .................... 215/307; 215/317; 356/246
[58] Field of Search ............... 206/459, 526; 215/307, 215/317, 321; 356/246

[56] References Cited

U.S. PATENT DOCUMENTS

| | | | |
|---|---|---|---|
| 2,949,204 | 8/1960 | Edwards | 215/321 |
| 2,990,076 | 6/1961 | Stull | 215/321 |
| 3,120,318 | 2/1964 | Rigor | 215/206 |
| 3,247,994 | 4/1966 | Madsen et al. | 215/321 |
| 3,362,556 | 1/1968 | Waldrum | 215/321 |
| 3,441,383 | 4/1969 | Mooke et al. | 356/246 |
| 3,607,098 | 9/1971 | Strande | 356/246 |
| 3,627,431 | 12/1971 | Komarniski | 356/246 |
| 3,680,967 | 8/1972 | Engelhardt | 356/246 |
| 3,696,957 | 10/1972 | Van Baarn | 215/321 |
| 3,715,063 | 2/1973 | Susuki et al. | 215/321 |
| 3,907,146 | 9/1975 | Fields | 215/321 |
| 3,976,196 | 8/1976 | Mueller | 206/326 |
| 3,983,999 | 10/1976 | Morton | 206/526 |
| 4,278,437 | 7/1981 | Haggar | 356/246 |
| 4,289,252 | 9/1981 | Helms | 215/321 |

Primary Examiner—David T. Fidei
Attorney, Agent, or Firm—Daniel Reitenbach

[57] ABSTRACT

A specimen receptacle assembly for clinical analyzer apparatus, such as an apparatus utilized in the testing of biological samples, as for instance, serum or other body fluid samples, to aid in the determination of, for instance, infectious diseases, metabolic state, or the like. The receptacle assembly comprises a cap formed as an arcuate segment having a plurality of generally vertically extending openings spaced lengthwise therealong, and a plurality of separate specimen cups, which are adapted to receive the specimen samples therein, together with means on the cap and on the cups for releasably attaching the cups to the cap as an assembly, whereby each of the openings in the cap provides access to the interior of a respective one of the cups from exteriorly of the cap. The attaching means includes a novel arrangement of cam surfaces and interlocking means on the cap and the cups, for snap-fastening of the cups to the cap, and yet providing for ready removal of the cups from the cap or vice versa, when it is desired to separate the same. The cups preferably have an enlarged mouth diameter on their upper ends, for facilitating filling by pouring, and have a bottom shape that minimizes the amount of residual fluid when aspirating the cup.

18 Claims, 3 Drawing Sheets

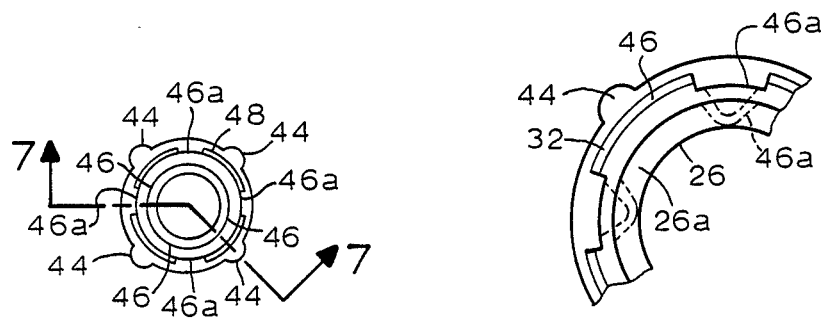
FIG. 6
FIG. 11
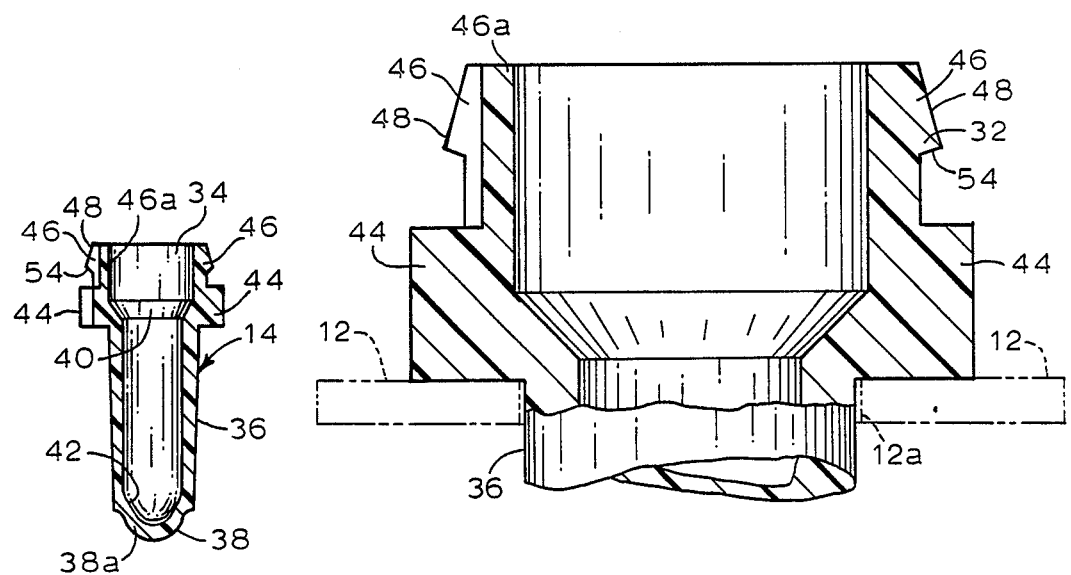
FIG. 7
FIG. 8

SPECIMEN CUP AND CAP ASSEMBLY FOR CLINICAL ANALYZER

This invention relates to analyzing apparatus in which fluid samples are to be tested, such as, for instance, biological samples used in the testing of certain body fluids or disease. More particularly, this invention relates to a receptacle assembly for holding the samples for testing by an analyzer apparatus. The receptacle assembly comprises a cap and plural cup structure which is particularly suitable for throwing away after being used once, and in that connection is preferably formed of inert plastic material.

BACKGROUND OF THE INVENTION

Many types of specimen receptacles are known in the art. Automatic analyzing apparatus for testing fluid samples are also well known in the art, including the utilization therewith of throw-away specimen cups formed of plastic, and having individual caps, adapted for snap attachment to the respective separate specimen cups and an associated cap, into the analyzing apparatus, and so far as applicant knows, heretofore such specimen cups and associated snap-on caps, have been provided as individual, separate articles, so that loading and unloading ]is quite time consuming and tedious. The individual prior art specimen cups have also been somewhat inadequate by reason 1 that they retain substantial residues of quantities of serum which is lost upon disposal of the cup which becomes substantially costly in mass testing procedures; also the prior art cups are impractical when limited quantities of serum are only available.

SUMMARY OF THE INVENTION

The present invention provides a specimen cap and cup receptacle assembly wherein a plurality of specimen cups can be readily and rapidly assembled with a strip-like cap that includes means adapted for snap-fastening coaction with a plurality of specimen cups, thus enabling the handling and/or transfer of a plurality of the specimen cups at one time, to and from a transport ring of the analyzer, or the like, thus materially shortening the time for loading and unloading such transport ring. Moreover, the present arrangement of specimen cup provides for minimizing the amount of residual fluid remaining in the respective specimen cup when the latter is aspirated, as by means of an automatic probe of the analyzer apparatus.

A novel arrangement of interlocking means, including cam means is provided on the individual specimen cups and on the associated cap strip, to facilitate the assembly of the cap strip with a plurality of the cups.

Accordingly, an object of the invention is to provide a novel specimen assembly for clinical analyzer apparatus, or the like and wherein a plurality of specimen cups can be expeditiously assembled and disassembled from a strip-type cap, for handling such plurality of specimen cups all at one time.

Another object of the invention is to provide a novel specimen assembly for clinical analyzer apparatus or the like, comprising a plurality of specimen cups assembled with a striplike cap arranged in arcuate segmental form.

A still further object of the invention is to provide a novel arrangement of strip-cap and specimen receptacle cup adapted for assembly, and wherein the specimen cups include a novel arrangement of the interlocking barbs and cam surfaces from the strip cap, to provide an expeditious snap-on and snapoff cap arrangement, that is sufficient to handle a considerable axial load, but wherein the cap can be still readily removed from the cups when so desired.

Another object of the invention is to provide an ]assembly of the above mentioned type wherein the cups are so constructed and arranged as to permit expeditious filling thereof by pouring, and wherein each of the cups has a bottom shape that minimizes the amount of residual fluid therein upon aspiration of the individual cup.

A still further object of the invention is to provide a novel assembly of the aforementioned type which can be thrown away after one usage thereof, thus obviating the necessity of cleaning and storing thereof for future use.

Other objects and advantages of the invention will be apparent from the following description taken in conjunction with the accompanying drawings wherein:

BRIEF DESCRIPTION OF THE DRAWINGS

FIG. 6 is a top plan view of the specimen cup per se of the assembly of FIGS. 2-5;

FIG. 7 is a vertical sectional view taken generally along the plane of line 7—7 of FIG. 6, looking in the direction of the arrows;

FIG. 8 is an enlarged, fragmentary illustration of the head or upper portion of the specimen cup of FIGS. 6 and 7, illustrating in greater detail the interlocking barbs and disassembly of the cup with the strip cap, and for holding the cup in assembled relationship with the cap;

FIG. 11 is an enlarged, fragmentary top plan illustration of the cup, and showing in phantom lines the flexure of the web structure of the upper portion of the cup during the inward bending or flexure movement of the interlocking barbs of the cup upon entry into the cap, and upon disassembly of the cup from the cap, to accomplish the snap-on connection thereof;

DESCRIPTION OF PREFERRED EMBODIMENT

Figure 1:
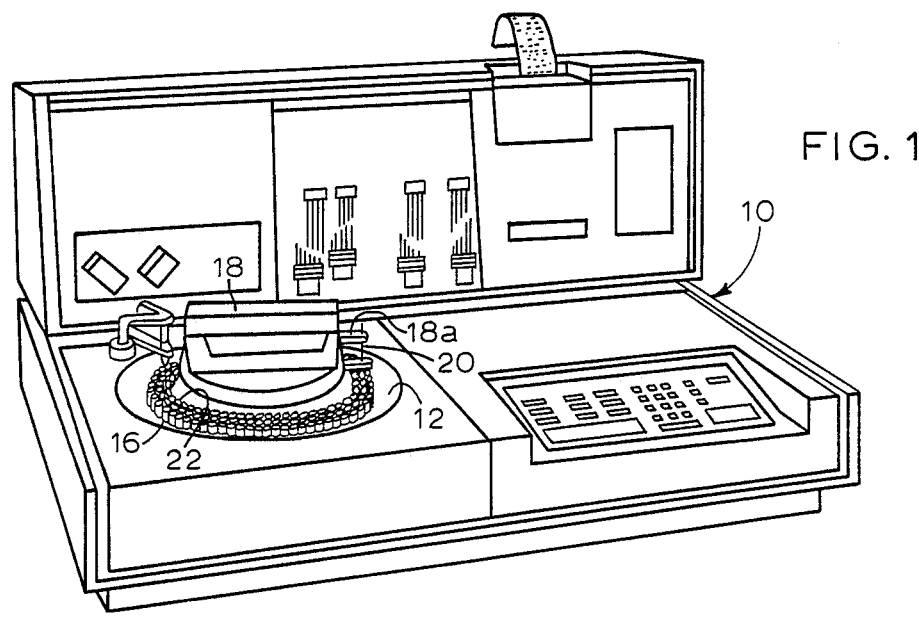
FIG. 1 is a perspective illustration of a clinical analyzer apparatus with which the specimen receptacle assembly of the invention may be used.
Figure 2:
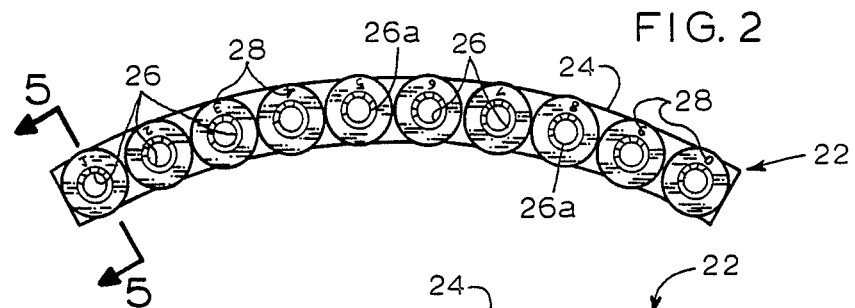
FIG. 2 is a top plan view of the specimen receptacle assembly of the invention.

FIG. 1 shows a perspective view of a clinical analyzer apparatus with which the specimen cup and cap assembly is related to the testing of biological samples such as for instance serum, but the present invention is not restricted to such type of analyzing. Such analyzer apparatus may be utilized for instance to provide for automatic testing of individual body fluid samples of a substantial number of patients suspected of having for example, some disease, such as for instance gonorrhea, and facilitates mass population screen testing.

Figure 3:
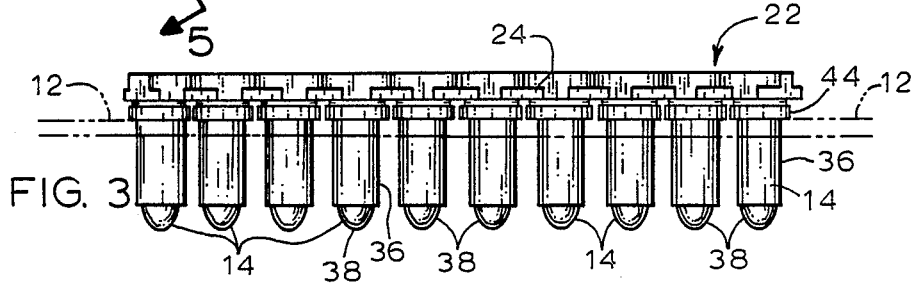
FIG. 3 is a front elevational view of the assembly illustrated in FIG. 2.
Figure 5:
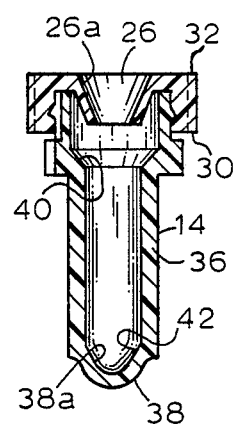
FIG. 5 is an enlarged, vertical sectional view taken generally along the plane of line 5—5 of FIG. 2, looking in the direction of the arrows.
Figure 4:
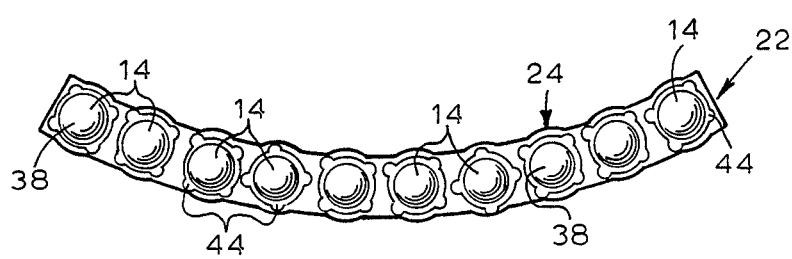
FIG. 4 is a bottom plan view of the specimen assembly illustrated in FIGS. 2 and 3.

Such apparatus conventionally includes a transport ring 12 which has a plurality of openings therein disposed in a circular pattern, for receiving for instance, specimen cups 14 (FIGS. 3 and 5) which are supported in such openings and contain the specimens to be analyzed by the apparatus. In the apparatus illustrated, the inner ring 16 of vessels are the specimen cups illustrated in connection with the invention. A rotatable and powered head 18 on the apparatus may include an arm 18a which is movably transversely with respect to the transport ring 12 and 11 which may include a vertically movable probe 20 for taking material from the respective serum cup. Apparatus 10 may be of the general type identified as an Impact 400 Analyzer, produced by the assignee of the present invention. Reference may also be had to U.S. Pat. No. 4,236,825 issued Dec. 2, 1980 to Saul R. Gilford, for an example of another type of analyzer which is adapted to perform the same general operations on specimens, utilizing however, a somewhat different and less sophisticated mode of operation as compared to the aforementioned Impact 400 type machine.

Referring now particularly to FIGS. 2-5, the present invention relates to a cap and cup assembly 22 for use in the analyzer of FIG. 1, but it will be understood that such invention may be utilized in other types of analyzers and other apparatus wherein it is an advantage to be able to handle a individually. Assembly 22 comprises a strip-like cap 24, having a plurality of the aforementioned specimen cups 14 removably secured thereto, as shown for instance in FIGS. 2-5. Cap 24 has a plurality of openings 26 extending therethrough and disposed in generally spaced relation lengthwise of the cap. The openings may have indicia 28, and in this instance numbers, associated therewith, for identifying the particular specimen cup opening. Each of the openings 26 is preferably defined by a funnel-like structure 26a extending downwardly from the top surface of the cap, for a purpose to be hereinafter described.

Figure 12:
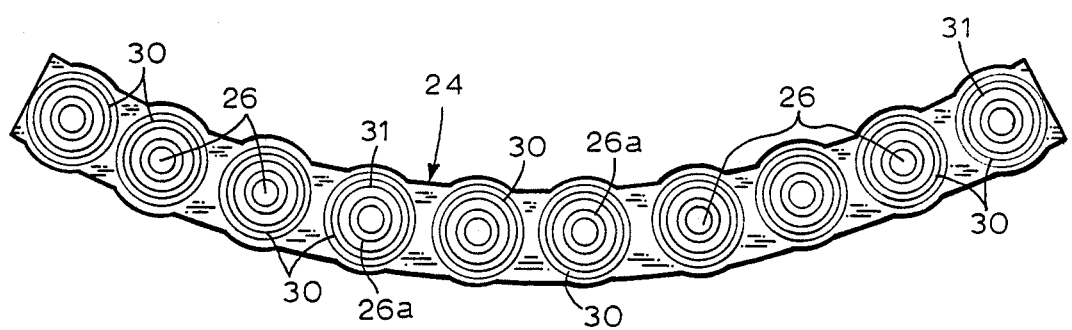
FIG. 12 is a bottom plan illustration of the cap member of the assembly of FIGS. 2-5.

Referring in particular to FIG. 12 which shows the bottom of the strip cap 24, there is associated with each of [the openings 26 in the cap, means 30 for interlocking the cups or vessels 14 to the strip cap in releasable relationship. Such means 30 provides a snap-fastening arrangement between the cap 24 and the cups 14.

Means 30, in the embodiment illustrated, comprises an inwardly extending shoulder 30a circumscribing the respective recess 31 in the cap receiving the upper end of the respective cup therein, and adapted for interlocking coaction with complementary fastening means 32 (FIGS. 9 and 10) on the cups 14, as will be hereinafter described in greater detail.

The strip cap 24 is preferably formed of plastic so that it may be thrown away after one usage thereof, and a suitable plastic material has been found to be medium impact ABS plastic. Such plastic material is preferably white for marker readability. The height H (FIG. 10) of the cap strip is such that provides adequate space for writing on the exterior side surfaces of the cap by the analyzer operator, and the plastic material is preferably of such type that such writing can be accomplished, utilizing conventional writing instrumentation. Likewise sufficient space is provided on the top surface to provide suitable indicia for identifying each individual cup, as aforesaid.

The vessels or cups 14 preferably comprise a widened mouth portion 34 (FIG. 7) which facilitates the pouring of a specimen into the cup, a stem or body portion 36 of elongated configuration, depending from the mouth portion 34, and a tip portion 38 which preferably has a highly polished spherical-like interior surface 38a cup as by aspiration from the cup, and thus minimizes the amount of residual fluid when the cup is aspirated, as for instance by the automatic probe 20. The mouth portion 34 is preferably connected to the stem or body portion 36 by inwardly sloping surface 40, and with the tip portion 38 being connected to the stem or body portion 36, on its interior surface by downwardly and inwardly sloping side wall surfaces 42, as best illustrated in FIG. 7. The cup 14 may have a plurality of circumferentially spaced protrusions 44 thereon, adapted to support the cup in an opening in a support surface, such as the aforementioned transport ring 12, and to prevent . said cup from falling through any hole in the transport ring 12.

Each cup is provided at its upper end with the aforementioned interlocking means 32, which in the embodiment illustrated comprise spaced barbs 46, connected with thin web sections 46a.

Each of the barbs 46 has a cam surface 48 thereon adapted for camming engagement with a complementary cam surface 50 (FIGS. 9 and 10) on the shoulder 30a of cap member 24, so as to cause inwardly flexing or general radial movement of the barbs during assembly of the cap onto cup or versa. Aforementioned cam surfaces 48 and 50 preferably slope at an angle of approximately 15° with respect to the vertical. During such general inward movement of the barbs during application of the cap (or the removal of the cap from the cup) the webs 46a flex or crease so as to permit the barbs 46 on the cup to pass the shoulder 30a on the cap until the barbs clear the shoulder, at which time they snap back onto their non-deformed positions and into snap-fastening coaction with the shoulder 30a on the cap, to interlock the cap and the cups together. In such interlocked condition, the top of the cap generally has clearance C (FIG. 9) at top to resist disengagement when bumped sideways and to provide overtravel to assure complete installation of all cups. The aforementioned funnel portion 26a, aids in preventing evaporation of the specimen contained in the respective cup, thus aiding in preserving the accuracy of the tests run thereon.

Figure 9:
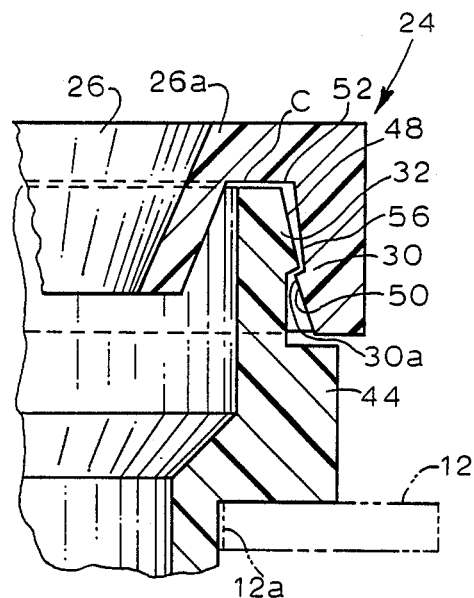
FIG. 9 is an enlarged, fragmentary illustration of the cup and cap in assembled condition.
Figure 10:
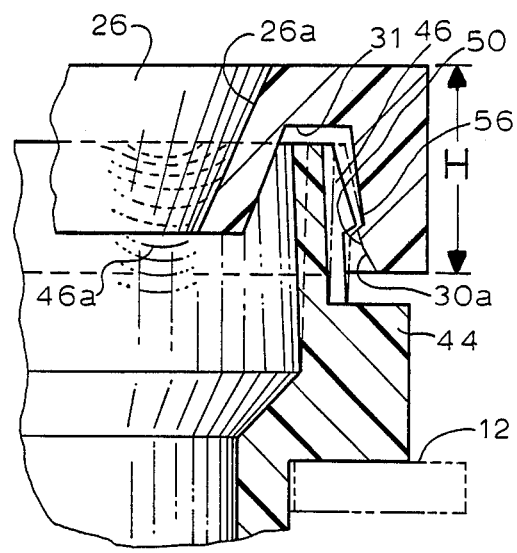
FIG. 10 is an enlarged, fragmentary illustration of the cup and cap during assembly of the cap onto an associated cup, and showing the generally radial inward flexure of the interlocking barbs on the upper end portion of the cup, due to the application of the cap to the cup. which permits the entry of the cups into interlocking coaction with the associated cap.

Each barb 46 on the cup preferably has a sloping undersurface 54 (FIG. 8) which is adapted for camming engagement the cap, so as to provide a directional engagement force, During disengagement, the barbs again swing or move inwardly against the resistance to creasing or crimping of the webs 46a until the head of the barbs on the cup move past the respective shoulder 30 on the cap, at which time the barbs swing back to their normal non-deformed position, as illustrated for instance in FIGS. 7, 8 and 9. Aforementioned surfaces 54 and 56 preferably slope at an angle of approximately 30° with respect to the horizontal.

The cups are preferably formed of plastic so that suitable material has been found to be polyethylene plastic, and a mixture of approximately 25% by weight of high density polyethylene and approximately 75% by weight of low density polyethylene has been found to be particularly suitable, for providing the cups of the invention with the desired flexibility. However, it will be understood that other mixtures and types of plastic materials may also be utilized.

The interlocking coaction between the shoulder means 30 on the cap with the interlocking means 32 on the cups, provides a sufficient connection to support the axial load of the specimen material disposed in the cups, and is such as to preferably provide for a minimum holding power of approximately 6.5 ounce axial load on the respective cup. Such an arrangement provides for maintenance of the assembly of the cap and the cups for the purposes to which they are adapted for use, and yet provides for ready separation of the cups from the cap or vice versa, when that is deemed desirable or necessary.

The rounded exterior configuration of the end tip of the cups facilitates the entry of the cap-cup assembly into the receiving openings in support plate, such as for instance the aforementioned transport plate 12 of the analyzer apparatus.

From the foregoing discussion and accompanying drawings it will be seen that the invention provides a novel specimen assembly of a cap and a plurality of specimen cups, for use in apparatus such as for instance a clinical analyzer apparatus, and wherein the cap comprises a strip-type cap having a plurality of openings therein with a plurality of cups assembled in snap-fastened relation to the cap, with each of the cups being disposed in coacting underlying relation with the respective of the openings in the cap. The invention also provides a novel specimen cup arrangement that permits expeditious filling of the cup by pouring, and which has a bottom shape that minimizes the amount of residual fluid when aspirating the cup. The cups and the strip cap have a novel arrangement of interlocking means for maintaining the cups in assembled relationship with the strip cap, but providing for ready disassembly therebetween when such is desirable or necessary. The invention also provides a throw-away cup and strip cap assembly which can be used only once if so desired, and then can be disposed of.

The terms and expressions which have been used are used as terms of description and not of limitation, and there is no intention in the use of such terms and expressions of excluding any equivalents of any of the features shown or described, or portions thereof, and it is recognized that various modifications are possible within the scope of the invention claimed.

What is claimed is:

1. A specimen cup and cap assembly for a clinical analyzer apparatus comprising a strip-like cap formed as an arcuate strip segment, in plan, having a plurality of generally vertically extended spaced openings therethrough spaced lengthwise of said strip segment and in generally evenly spaced relation between the sides thereof, a plurality of separate specimen cups, and means on said cap and on each said cups for releasably attaching said cups to said cap as an assembly, whereby each of said openings provide access to the interior of a respective one said cups from exteriorly of said cap, said openings being adapted to provide access for an automatic probe of an associated clinical analyzer apparatus.

2. An assembly in accordance with claim 1 wherein each of said cups has an upper portion comprising said attaching means and possessing general flexibility so that said cup can be snapped into and out of holding coaction with said cap upon respectively upward and downward or sidewise force applied to said cup.

3. An assembly in accordance with claim 2 wherein said upper portion of said cup is formed of polyethylene plastic, said upper portion possessing memory but being deformable generally radially inwardly to permit said snap fastening entry and/or removal of said cup from said cap or vice versa.

4. An assembly in accordance with claim 2 wherein said upper portion comprises a plurality of peripherally spaced projections thereon, each of which has cam surface means adapted for camming coaction with generally complementary cam surface means on said cap for causing said inward deformation of said upper portion of said cup with respect to said cap and entry of said cup into snapped fastened coaction relation with said cap.

5. An assembly in accordance with claim 2 wherein said upper portion comprises cam means spaced circumferentially about the periphery of said cup and connected by flexible webs and with said circumferentially spaced cam means being connected by flexible web means, said cap having complementary cam means thereon adapted for camming coaction with said cam means on said cup so as to force the cam means on said cup generally radially inwardly to cause generally radial folding of said webs until said cam means on said cap and said cup pass one another at which time said webs and cam means on said cup are adapted to spring back into their original orientation to cause said attaching means to interlock said cup with said cap. L 6. An assembly in accordance with claim 1 wherein said cap is formed of medium impact ABS plastic.

7. An assembly in accordance with claim 1 including laterally projecting protrusions on each of said cups intermediate the upper and lower extremities of said cup, adapted for engagement with a support ring of the apparatus.

8. An assembly in accordance with claim 1 wherein each of said cups comprises a widened entry portion at its upper end which can be conveniently poured into, and a narrower stem portion depending from said entry portion.

9. An assembly in accordance with claim 1 wherein the lower tip of each of said cups comprises a highly polished spherical configuration at its extremity to facilitate the removal of solution from the respective cup by aspiration.

10. An assembly in accordance with claim 1 including indicia on said cap member for identifying the openings in said cap member with a particular specimen placed therein.

11. An assembly in accordance with claim 1 wherein each said cup member comprises a mouth portion opening upwardly, a stem portion depending from said mouth portion and a lower distal tip portion extending downwardly from said stem 1 portion, said portions defining a cavity adapted to receive a specimen therein, said mouth portion being wider as compared to the width of said stem portion, and said tip portion having an interior bottom surface which is of generally spherical configuration with said recess defined by said cup diminishing in width from the upper extremity of said mouth portion to the lower end of said tip portion, with the exterior end of said tip portion being of convergingly tapered configuration in a downward direction.

12. An assembly in accordance with claim 4 wherein the juncture of said mouth portion with said stem portion is defined by a sloping surface extending in converging relationship in a downward direction.

13. An assembly in accordance with claim 5 wherein said cam means on said upper portion of said cup is disposed at an angle of approximately 15 degrees with respect to the vertical and slopes in a direction upwardly and inwardly toward the axis of said cup and wherein said cam for means on said cup is disposed at an angle of approximately 15 degrees with respect to the vertical and extends in an upward and inward direction from the horizontal.

14. An assembly in accordance with claim 5 wherein said cam means on said cap is disposed at an angle of approximately 15° with respect to the vertical and with said cap cam means diverging in a downward and outward direction with respect to the cam means on said cup.

15. An assembly in accordance with claim 2 wherein said attaching means on said cup includes an interlock surface disposed at an angle of approximately 30° with respect to the horizonal and which diverges in a downward and inward direction, said cup having a complementary arranged interlock surface adapted for surface-to-surface engagement with said interlock surface [on said cap.

16. A cap adapted for assembly with a plurality of specimen cups for use for instance in a clinical analyzer apparatus, said cap comprising a strip of material formed as an arcuate strip segment, in plan, having a plurality of generally vertically extending openings therethrough spaced lengthwise of said strip segment and in generally evenly spaced relation between the sides thereof, and means on the underside of said cap for releasably attaching a plurality of associated cups to the cap as an assembly, said means coacting with each of said openings for orienting a respective cup in communicating relation with the respective of said openings in said cap from exteriorly of said cup.

17. A cap in accordance with claim 16 wherein each of said openings is defined by an inverted truncated conical portion and said means comprises a shoulder coacting with the respective opening adapted for interlocking an associated cup to the underside of the cap.

18. A cap in accordance with claim 17 formed of opaque plastic material, said cap having a defining exterior side wall depending below said conical portions defining said openings therethrough, said plastic being able to be written upon by conventional writing instrumentalities.

* * * * *